United States Patent [19]

Ebmeyer et al.

[11] Patent Number: 5,723,662
[45] Date of Patent: Mar. 3, 1998

[54] PROCESS FOR PREPARING A PARTICULARLY PURE GLYCOLIC ACID

[75] Inventors: Frank Ebmeyer, Augsburg; Harald Häberlein, deceased, late of Neusäss; by Hans Harald Häberlein, heir, Neu-Ulm; by Jörg Thomas Häberlein, heir, Allersberg; by Mark Christian Häberlein, heir, Freiburg; Holger Mohn, Gelnhausen-Hailer, all of Germany

[73] Assignee: Hoechst Aktiengesellschaft, Germany

[21] Appl. No.: 780,983

[22] Filed: Jan. 9, 1997

[30] Foreign Application Priority Data

Jan. 10, 1996 [DE] Germany ............ 196 00 620.1

[51] Int. Cl.⁶ .................................................. C07C 59/00
[52] U.S. Cl. ........................................................ 562/579
[58] Field of Search ................................. 562/550, 579

[56] References Cited

FOREIGN PATENT DOCUMENTS

| | | |
|---|---|---|
| 0194038 | 1/1908 | Germany . |
| 1254615 | 11/1967 | Germany . |
| 2812682 | 10/1979 | Germany . |
| 2812683 | 10/1979 | Germany . |
| WO 92/05138 | 4/1992 | WIPO . |

*Primary Examiner*—Paul J. Killos
*Attorney, Agent, or Firm*—Connolly and Hutz

[57] ABSTRACT

The present invention relates to a process for preparing a particularly pure glycolic acid by saponification with chloroacetic acid with an excess of alkali metal hydroxide, with the resulting alkali metal chloride being filtered off, and the 20 to 70% strength by weight glycolic acid solution being subsequently subjected to an electrodialysis at 20° to 40° C. and a cell voltage of 0.5 to 2.5 V per cell pair. The process of the invention permits optimum removal of sodium chloride and chloroacetic acid as necessary for preparing a particularly pure glycolic acid. Other organic acids, nitrogen compounds, aldehydes and salts are not produced in this process and thus do not affect the product quality.

3 Claims, No Drawings

PROCESS FOR PREPARING A PARTICULARLY PURE GLYCOLIC ACID

The invention describes a process for preparing a particularly pure glycolic acid, the purity relating to the greatest possible freedom from impurities such as alkali metal chlorides, organic acids, aldehydes, nitrogen compounds and salts of any type. A high-quality glycolic acid of this type is used in the pharmaceutical industry and in the cosmetics industry.

This purity cannot be achieved by simple distillation or crystallization. Distillation is excluded, since glycolic acid decomposes during this. Satisfactory purification does not occur during crystallization, since the above impurities such as salts and organic acids crystallize out with the glycolic acid or remain adhering to it.

The preparation of glycolic acid by saponification of chloroacetic acid with alkali metal hydroxides has been disclosed, substantial removal of the resulting sodium chloride being able to be achieved by filtration and subsequent precipitation of the sodium chloride remaining in solution by addition of methyl ethyl ketone or methyl isobutyl ketone. The organic solvent is then distilled off (DE-A-28 12 682, DE-A-28 12 683). The disadvantage of this process is in the use of an organic solvent and in that organic impurities cannot be removed in this manner.

The preparation of glycolic acid by carbonylation of formaldehyde has likewise been disclosed (WO 92/05138). However, substantial amounts of the components arising as impurities, in particular formaldehyde, formic acid and methoxyacetic acid, remain in the product. Processes using ion exchangers can also be employed to remove salts. However, the necessary regeneration of the ion exchangers makes this process very laborious and in addition produces wastewaters from the regeneration.

The preparation of glycolic acid by electrochemical reduction of oxalic acid is also described (DE 194 038). Producing a particularly pure product is also difficult in this process, since the by-product glyoxylic acid which behaves in a very similar manner chemically, and also unreacted oxalic acid, make it difficult to produce high-purity quality grades.

The preparation of glycolic acid by hydrolysis of the glyconitrile, which is produced by reacting formaldehyde with prussic acid, is also described (DE-A-1254615). In this case, the nitrogen compounds arising in the hydrolysis, in particular ammonium salts, are very difficult to separate off, which makes producing a high-purity quality grade difficult.

The object of the present invention was thus to provide a process which can be implemented on the industrial scale for preparing a particularly pure glycolic acid and which does not have the disadvantages described above.

Surprisingly, it has now been found that a particularly pure glycolic acid is obtained by saponification of chloroacetic acid with an excess of alkali metal hydroxide, with the resulting alkali metal chloride being filtered off, if the 20 to 70% strength by weight glycolic acid solution is subsequently subjected to an electrodialysis at 20° to 40° C. and a cell voltage of 0.5 to 2.5 V per cell pair.

The saponification is carried out with an alkali metal hydroxide excess of 0 to 10, preferably 2 to 8% by weight. Of the alkali metal hydroxides, NaOH or KOH have proved to be particularly suitable. The saponification is advantageously carried out at a temperature of 100° to 160° C., in particular 110° to 150° C. and at a gauge pressure of 0 to 10, in particular 0 to 5, bar. After the saponification, only traces of chloroacetic acids remain in the saponification product, subsequently, after filtering off the resulting alkali metal chloride, an electrodialysis achieves a very great degree of desalting of the solution and a further decrease in concentration of the chloroacetic acids.

The filtration which already removes the majority of the sodium chloride is divided between saponification and electrodialysis. As a result it is possible to recycle to the saponification the salt concentrate arising in the electrodialysis. No process-specific wastewater is thus produced.

The further purification by electrodialysis is made possible by an excess of alkali metal hydroxide being used in the saponification, which excess remains in the saponification process. Since chloroacetic acids are stronger acids than glycolic acid, these are therefore present in the saponification product in the ionized state as alkali metal carboxylates and can be removed by electrodialysis.

The electrodialysis is carried out at a temperature of 20° to 40° C., for example. The glycolic acid concentration in the diluate in this case is advantageously 20 to 70, in particular 40 to 60, % by weight. An applied cell voltage of 0.5 to 2.5 V has proved to be suitable, in particular 1 to 2 V.

The process of the invention permits optimum removal of sodium chloride and chloroacetic acid as necessary for preparing a particularly pure glycolic acid. Other organic acids, nitrogen compounds, aldehydes and salts are not produced in this process and thus do not affect the product quality.

Example 1 shows a procedure according to the process of the invention by which the impurities chloroacetic acid and dichloroacetic acid can no longer be detected within the product within a detection limit of 10 ppm.

After the electrodialysis, a little water is removed from the solution by distillation and the glycolic acid concentration is set to the desired value, customarily 70% by weight.

The invention is described by the examples below in which the electrodialysis is carried out under the following conditions:

A laboratory apparatus from Berghof (Bel 2) is used, having a membrane stack, fitted with 10 cell pairs arranged parallel, comprising anion- and cation-exchange membranes (manufacturer, Asahi Glass Co. Ltd.). The effective membrane area is 37 cm$^2$. The electrodes are made of platinum-coated titanium. An electrical voltage of 1.5 V per cell pair is applied and a flow of approximately 5 cm/s is passed over the membranes. The apparatus has 3 circulating streams. The diluate circuit stream contains the glycolic acid solution to be desalted. The aqueous concentrate stream serves to receive the salt. The electrode flushing solution ($Na_2SO_4$, 0.2% strength by weight) prevents undesired electrode reactions, such as anodic $Cl_2$ development. The experimental temperature is 20° to 40° C. All percentages in the examples are by weight.

EXAMPLES

Example 1

1.00 kg of 50% strength sodium hydroxide solution (7.5% excess) is added to 1.10 kg of chloroacetic acid having a dichloroacetic acid content of 300 ppm and the mixture is heated at 115° C. for 70 h. 0.52 kg of sodium chloride are then removed by filtration and 0.10 kg of water by distillation. 1.41 kg of 55% strength aqueous glycolic acid remain, which contains 11% of sodium chloride and less than 100 ppm of chloroacetic acid. This solution is fed on the diluate side to the electrodialysis. 1.41 kg of 0.25% strength sodium chloride solution being charged on the concentrate side. Over the experimental period of 30 h, the voltage is kept constant at 15 V. The average electrical current is approximately 0.6 A. The conductivity of the diluate solution decreases from 18 to 5 mS/cm and increases in the concentrate from 5 to 110 mS/cm. 1.21 kg of aqueous glycolic acid solution having an acid content of 52% and chloroacetic acid and dichloroacetic acid contents of less than 10 ppm are obtained. From this solution, by removing 0.31 kg of water, a 70% strength glycolic acid solution is prepared. The content of chloroacetic acid and dichloroacetic acid is less than 10 ppm, and the sodium chloride content is 0.02%.

Example 2

880 kg of sodium hydroxide solution (4% excess) are added to 1250 kg of 80% strength aqueous chloroacetic acid solution having a dichloroacetic acid content of 240 ppm and the mixture is heated in a reactor at 145° C. at a pressure of 1.8 bar for 20 h. 476 kg of sodium chloride are filtered off and 360 kg of water are distilled off. 1282 kg of 56% strength glycolic acid solution remain, which contains 13% of sodium chloride and 500 ppm of chloroacetic acids. 4.3 kg of this solution are fed on the diluate side to the electrodialysis, 5 kg of 0.25% strength sodium chloride solution being charged on the concentrate side. Over the experimental period of 54 h, the voltage is kept constant at 15 V. The average electrical current is approximately 0.6 A. The conductivity of the diluate solution decreases from 20 to 4 mS/cm and increases in the concentrate from 5 to 120 mS/cm. 3.1 kg of aqueous glycolic acid solution having an acid content of 57.3%, 0.016% of NaCl and a content of chloroacetic acids of 380 ppm are obtained. From this solution, by removing 0.59 kg of water, a 70% strength glycolic acid solution is prepared.

Example 3

The procedure of Example 2 is followed, but only 868 kg of 50% strength sodium hydroxide solution (2.5% excess) are used. After filtering off the salt, a solution which contains 57% of glycolic acid and 0.32% of chloroacetic acid and 11.3% of NaCl is obtained. 4 kg of this solution are thus fed on the diluate side to the electrodialysis, 4 kg of 0.25% strength sodium chloride solution being charged on the concentrate side. Over the experimental period of 48 h, the voltage is kept constant at 15 V. The average electrical current is approximately 0.6 A. The conductivity of the diluate solution decreases from 31 to 3 mS/cm and increases in the concentrate from 5 to 115 mS/cm. 2.9 kg of aqueous glycolic acid solution having an acid content of 50.7%, 0.004% of NaCl and a content of chloroacetic acid of 0.13% are obtained. From this solution, by removing 0.76 kg of water, a 70% strength glycolic acid solution is prepared. The content of chloroacetic acids is 1300 ppm, and the sodium chloride content is 0.004%

Example 4

The procedure of Example 2 is followed, but an 80% strength aqueous chloroacetic acid solution having a dichloroacetic acid content of 0.25% is used. After filtering off the salt, a solution which contains 56% of glycolic acid, 560 ppm of chloroacetic acids and 13% of NaCl is obtained. 4 kg of this solution are fed on the diluate side to the electrodialysis, 4 kg of 0.25% strength sodium chloride solution being charged on the concentrate side. Over the experimental period of 50 h, the voltage is kept constant at 15 V. The average electrical current is approximately 0.6 A. The conductivity of the diluate solution decreases from 21 to 3 mS/cm and increases in the concentrate from 4 to 120 mS/cm. 3 kg of aqueous glycolic acid solution having an acid content of 59.5% and containing 0.012% of NaCl and 320 ppm of chloroacetic acids is obtained. From this solution, by removing 0.42 kg of water, a 70% strength glycolic acid solution is prepared. The content of chloroacetic acid is 220 ppm, and the sodium chloride content is 0.012%.

It is claimed:

1. A process for preparing a particularly pure glycolic acid by saponification with chloroacetic acid with an excess of alkali metal hydroxide, with the resulting alkali metal chloride being filtered off, which comprises subsequently subjecting the 20 to 70% strength by weight glycolic acid solution to an electrodialysis at 20° to 40° C. and a cell voltage of 0.5 to 2.5 V per cell pair.

2. The process as claimed in claim 1, wherein the glycolic acid concentration in the diluate is 40 to 60% by weight.

3. The process as claimed in claim 1, wherein the applied cell voltage in the electrodialysis is 1 to 2 V per cell pair.

* * * * *